(12) United States Patent
McClellan (10) Patent No.: US 11,207,149 B2
(45) Date of Patent: Dec. 28, 2021

(54) THERMAL MRI SAFE TISSUE EXPANDER PORT

(71) Applicant: William T. McClellan, Morgantown, WV (US)

(72) Inventor: William T. McClellan, Morgantown, WV (US)

( * ) Notice: Subject to any disclaimer, the term of this patent is extended or adjusted under 35 U.S.C. 154(b) by 403 days.

(21) Appl. No.: 16/415,563

(22) Filed: May 17, 2019

(65) Prior Publication Data

US 2019/0350664 A1 Nov. 21, 2019

Related U.S. Application Data

(60) Provisional application No. 62/672,640, filed on May 17, 2018.

(51) Int. Cl.
| | | |
|---|---|---|
| A61B 90/00 | (2016.01) | |
| A61B 17/00 | (2006.01) | |

(52) U.S. Cl.
CPC .............. *A61B 90/02* (2016.02); *A61B 17/00* (2013.01); *A61B 2017/00557* (2013.01); *A61B 2017/00792* (2013.01); *A61B 2017/00796* (2013.01); *A61B 2017/00911* (2013.01)

(58) Field of Classification Search
CPC ............ A61F 2/12; A61B 90/00; A61B 90/02
See application file for complete search history.

(56) References Cited

U.S. PATENT DOCUMENTS

| | | |
|---|---|---|
| 4,671,255 A | 6/1987 | Dubrul et al. |
| 4,800,901 A | 1/1989 | Rosenberg |
| 5,630,843 A | 5/1997 | Rosenberg |
| 5,944,023 A | 8/1999 | Johnson et al. |
| 6,044,297 A | 3/2000 | Sheldon et al. |
| 6,206,930 B1 | 3/2001 | Burg et al. |
| 6,666,893 B2 | 12/2003 | Burg et al. |
| 7,575,597 B2 | 8/2009 | Rehnke |
| 7,736,391 B2 | 6/2010 | Schwibner et al. |
| 7,871,438 B2 | 1/2011 | Corbitt |
| 8,015,977 B2 | 9/2011 | Bertrand et al. |
| 8,387,817 B1 | 3/2013 | Zelechonok |
| 8,454,690 B2 | 6/2013 | McClellan |

(Continued)

FOREIGN PATENT DOCUMENTS

| | | |
|---|---|---|
| WO | 2011/063349 | 5/2011 |
| WO | 2011/075731 | 6/2011 |
| WO | 2018/078446 | 5/2018 |

OTHER PUBLICATIONS

Hawkin et al., "MRI Safety Information", Zimmer Biomet, http://www.zimmerbiomet.com/medical-professionals/support/mri.html, accessed Feb. 8, 2018; 3 pages.

*Primary Examiner* — Jason-Dennis N Stewart
(74) *Attorney, Agent, or Firm* — Andrew D. Wright; Roberts Calderon Safran & Cole, P.C.

(57) ABSTRACT

Improvements for use with tissue expanders are provided. A tissue expander includes: a selectively inflatable and deflatable shell that is configured to be implanted; and an access port for selectively inflating and deflating the shell, the access port comprising a sidewall, a base at a first end, and a membrane at a second end opposite the first end wherein the sidewall and the base of the access port are constructed of a material that is non-reactive with a magnetic resonance imaging (MRI) machine; and a structure of the access port is composed of a material that has a rate of temperature change lower than that of human tissue.

10 Claims, 4 Drawing Sheets

(56) References Cited

U.S. PATENT DOCUMENTS

| | | |
|---|---|---|
| 9,144,488 B2 | 9/2015 | Boyden et al. |
| 9,268,915 B2 | 2/2016 | Holmes et al. |
| 9,333,071 B2 | 5/2016 | Boyden et al. |
| 9,814,566 B1 | 11/2017 | Cree |
| 10,010,404 B2 | 7/2018 | McClellan |
| 10,252,145 B2 | 4/2019 | Tran et al. |
| 2005/0061198 A1 | 3/2005 | Khan et al. |
| 2007/0233273 A1 | 10/2007 | Connell |
| 2007/0288095 A1 | 12/2007 | Wirtel et al. |
| 2008/0033471 A1 | 2/2008 | Paz et al. |
| 2008/0091175 A1 | 4/2008 | Frikart et al. |
| 2008/0161929 A1 | 7/2008 | McCormack et al. |
| 2009/0012372 A1 | 1/2009 | Burnett et al. |
| 2009/0157180 A1 | 6/2009 | Schraga |
| 2010/0256775 A1 | 10/2010 | Belhe et al. |
| 2011/0153017 A1 | 6/2011 | McClellan |
| 2011/0208311 A1 | 8/2011 | Janowski |
| 2012/0041305 A1 | 2/2012 | Grissom et al. |
| 2012/0184893 A1 | 7/2012 | Thompson et al. |
| 2012/0302874 A1 | 11/2012 | Hollstien |
| 2013/0190796 A1 | 7/2013 | Tilson et al. |
| 2013/0325120 A1 | 12/2013 | McClellan |
| 2013/0338769 A1 | 12/2013 | Boyden et al. |
| 2014/0121771 A1 | 5/2014 | Chitre et al. |
| 2016/0066979 A1 | 3/2016 | Mueller et al. |
| 2016/0250017 A1 | 9/2016 | McClellan |
| 2016/0310306 A1 | 10/2016 | Brister et al. |
| 2017/0228627 A1 | 8/2017 | Geissler et al. |
| 2017/0246019 A1 | 8/2017 | Miesse et al. |

THERMAL MRI SAFE TISSUE EXPANDER PORT

FIELD OF THE INVENTION

The invention generally relates to medical devices and associated methods of manufacture and use, and more particularly to tissue expanders.

BACKGROUND

Breast reconstruction with a tissue expander (TE) is currently the most common technique used for breast reconstruction. Typically immediately after the female has a mastectomy the reconstructive medical professional places a tissue expander which serves to stretch the skin and muscle in order to make room for a future implant or maintain the existing skin envelope. Prosthetic reconstruction of the breast, as a staged procedure with tissue expanders followed by implants, is a reliable method for breast reconstruction that offers favorable aesthetic and psychological results while adding only minimal additional surgical intervention. Today, the process usually involves the placement of a tissue expander under the pectoralis major muscle and remaining skin of the absent breast. The tissue expander is then gradually inflated over several weeks or months by periodic injections of saline, causing the stretching and expansion of the overlying skin and muscle coverage. When adequate coverage is achieved, the tissue expander is typically removed, and a permanent breast implant is placed into the expanded space.

Conventional tissue expanders include a shell and a port for selectively inflating and deflating the shell. The port includes a metal structure supporting a membrane that can be pierced by a needle to facilitate the inflating and deflating of the shell. Because the tissue expander is implanted under the patient's skin, the surgeon (or other medical professional) cannot visually see the port when attempting to access the port with a needle. Accordingly, a magnet may be included in the structure of the port, and the surgeon may use a dangle-magnet that is external to the patient to attempt to locate the port that is internal to the patient via the magnetic attraction between the dangle-magnet and the magnet included in the structure of the port. However, the magnet included in the structure of the port, and the metal structure of the port itself, can interact with a magnetic resonance imaging (MRI) and cause problems. For example, the MRI may cause heating of the magnet included in the structure of the port and this heating can lead to pain for the patient. The interaction between the MRI and the magnet can also cause movement of the magnet, and this can lead to dislodgement and/or rupture of the tissue expander with in the patient. Moreover, the interaction of the MRI and the metal structure of the port itself can cause unwanted artifacts in the output of the MRI. For these reasons, tissue expanders are contraindicated for use with MRI's.

SUMMARY

In a first aspect of the invention, there is a tissue expander comprising: a selectively inflatable and deflatable shell that is configured to be implanted; and an access port for selectively inflating and deflating the shell, the access port comprising a sidewall, a base at a first end, and a membrane at a second end opposite the first end wherein the sidewall and the base of the access port are constructed of a material that is non-reactive with a magnetic resonance imaging (MRI) machine; and a structure of the access port is composed of a material that has a rate of temperature change lower than that of human tissue.

In another aspect of the invention, there is a tissue expander, comprising: a selectively inflatable and deflatable shell that is configured to be implanted; and an access port for selectively inflating and deflating the shell, the access port comprising a sidewall, a base at a first end, and a membrane at a second end opposite the first end, wherein the sidewall and the base of the access port are constructed of a material that is non-reactive with a magnetic resonance imaging (MRI) machine; and a structure of the access port comprises a portion having a specific heat capacity greater than 3.47 kJ/(kg*K).

In another aspect of the invention, there is method comprising: bringing a tissue expander into thermal equilibrium with surrounding tissue in which the tissue expander is implanted, wherein the tissue expander comprises: a selectively inflatable and deflatable shell that is configured to be implanted; and an access port for selectively inflating and deflating the shell, the access port comprising a sidewall, a base at a first end, and a membrane at a second end opposite the first end, wherein the sidewall and the base of the access port are constructed of a material that is non-reactive with a magnetic resonance imaging (MRI) machine, and a structure of the access port is composed of a material that has a rate of temperature change lower than that of human tissue. The method comprises: applying external cooling to the surrounding tissue; based on the external cooling, detecting the structure using an infrared sensor; and inserting a needle into the access port while using the infrared sensor as a guide.

In embodiments, there is a tissue expander with an MRI safe port that has no metal or other materials that produce unwanted artifacts in an MRI system. The port may be a polymer port that cannot be punctured by a needle. The port may have a coating or a composition that will accept or retain heat, such that a user can heat the ski with a hot pad thermally charge the port (or the port retains body heat and is always thermally charged). When the port is thermally charged, a user can cool the skin of the patient in which the tissue expander is implanted, thus exposing in infrared the still relatively hot port underneath the skin. As a result the, relatively hot port is locatable using an infrared camera. In some embodiments, the port is configured to not heat above 100° F. or below 80° F.

BRIEF DESCRIPTION OF THE SEVERAL VIEWS OF THE DRAWINGS

The present invention is described in the detailed description which follows, in reference to the noted plurality of drawings by way of non-limiting examples of exemplary embodiments of the present invention.

DETAILED DESCRIPTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

According to aspects of the invention, a tissue expander is constructed entirely of non-magnetic material(s), and at least a portion of the tissue expander has a rate of temperature change lower than that of the tissue surrounding the tissue expander. In embodiments, a portion of the tissue expander port has a heat capacity (or a specific heat capacity) that is different than the nominal heat capacity (or the nominal specific heat capacity) of the human body. In particular embodiments, the portion of the tissue expander port has a heat capacity (or a specific heat capacity) that is higher than the nominal heat capacity or (the nominal specific heat capacity) of the human body. In this manner, the portion of the tissue expander port exhibits a slower rate of cooling than that of the patient tissue surrounding the implanted tissue expander, such that the tissue expander port may be located using an infrared sensor that is external to the patient body in which the tissue expander is implanted. By constructing the entire tissue expander from non-magnetic material(s), the inventive tissue expander port is safe for use with an MRI, in contrast to conventional tissue expanders that are contra-indicated for use with MRI's. In this manner, implementations of the invention provide improvements in tissue expander technology and application.

Figure 1:
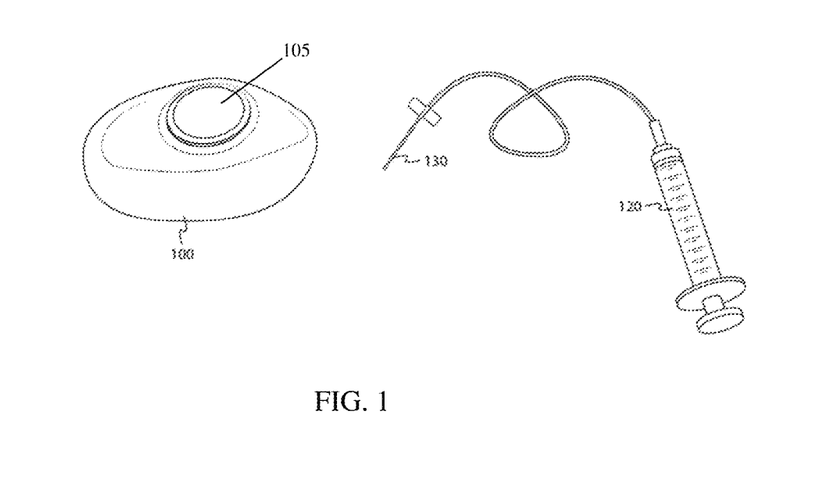
FIG. 1 shows a system used for tissue expansion, which may include a tissue expander and a fluid delivery system.

FIG. 1 shows a system used for tissue expansion, which may include a tissue expander 100 and a fluid delivery system 120. The tissue expander 100 includes an access port 105 (also called an implant port). The fluid delivery system 120 may include a needle 130 or other end used to access the interior of the tissue expander 100. The fluid delivery system 120 may provide a fluid to the interior (e.g., internal cavity defined by an implant shell 115) of the tissue expander 100 to cause the tissue expander 100 to expand. In some embodiments, the fluid delivery system 120 may also be used to access the interior of the tissue expander 100 to remove fluid from the tissue expander 100, which may cause the tissue expander 100 to contract or deflate.

Figure 2:
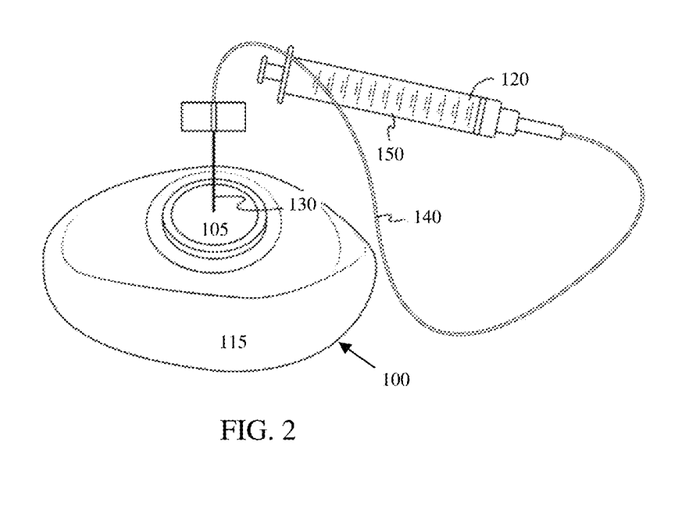
FIG. 2 shows an example of a fluid delivery system providing access to an access port of a tissue expander.

FIG. 2 shows an example of a fluid delivery system 120 providing access to an access port 105 of a tissue expander 100 comprising an implant shell 115. The fluid delivery system 120 may include a needle 130 and a tube 140 to provide fluid to the interior of the tissue expander 100 via the access port 105 (e.g., inflation/deflation port). The needle may puncture the access port 105 to provide fluid to, or remove fluid from, the interior (e.g., internal cavity) of the tissue expander. The access port 105 may be provided with a self-healing/sealing material that, after being punctured by a needle of the fluid delivery system 120, reforms an airtight and liquid tight seal. In some instances, the fluid delivery system 120 may utilize a tip other than a needle that may be capable of delivering a fluid to, and removing fluid from, the tissue expander 100.

A pressure differential may be created to cause fluid to flow into or out of the tissue expander 100. For example, a positive pressure may be provided from outside the tissue expander 100, which positive pressure causes inflation of the tissue expander 100. In one example, a syringe 150 may be used to provide the positive pressure. In another example, a negative pressure may be provided from within the tissue expander 100 to draw fluid out of the tissue expander 100 for deflation of the tissue expander 100. Alternatively, pumps or valves may be utilized to assist with fluid flow.

Figure 3:
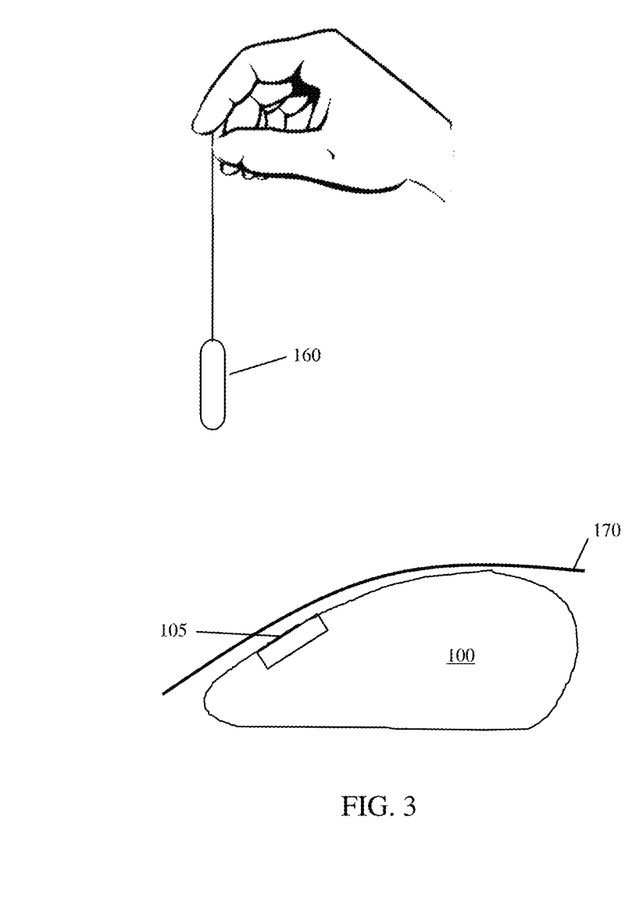
FIGS. 3 and 4 illustrate a method of locating a port of the tissue expander using a dangle-magnet.
Figure 4:
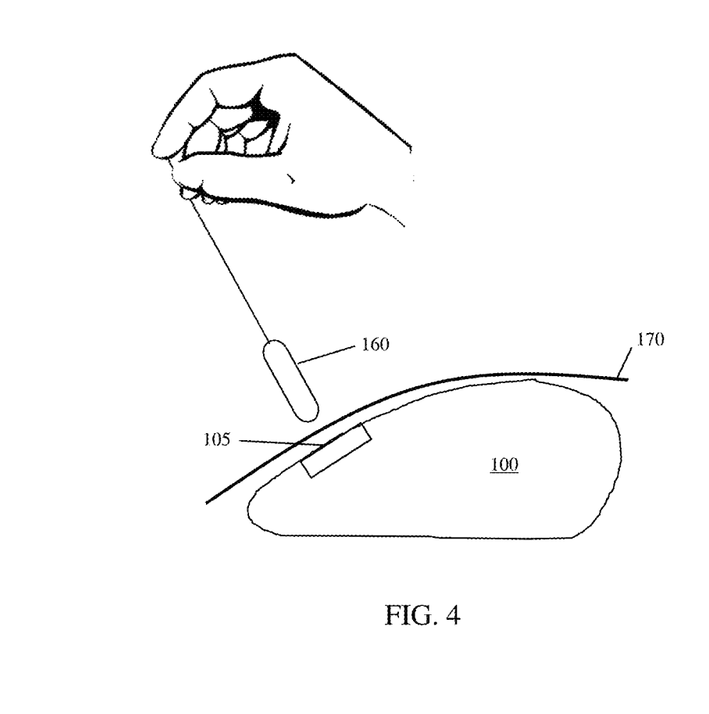

FIGS. 3 and 4 illustrate a method of locating the port 105 of the tissue expander 100 using a dangle-magnet 160. As shown in FIG. 3, the tissue expander 100 is implanted in a patient under the skin 170 of the patient. In this implanted state, a surgeon cannot visually see the port 105 because the port 105 is covered by the skin 170. Accordingly, the port 105 may be provided with a relatively magnet, and the surgeon may utilize an external dangle-magnet 160 to locate the port 105 via magnetic attraction between the magnet and the dangle-magnet 160. As depicted in FIGS. 3 and 4, the dangle-magnet 160 is drawn toward the port 105 when the dangle-magnet is moved within close proximity of the port 105, i.e., by the magnetic attraction force between the magnet and the dangle-magnet 160. In this manner, the surgeon may use the use the dangle-magnet 160 to locate the port 105. However, this method has drawbacks of being imprecise and requiring the use of a relatively large/magnet at the port 105. In particular, the magnet included in the structure of the port 105, and the metal structure of the port 105, can interact with and cause problems in a magnetic resonance imaging (MRI) system. For example, the MRI may cause heating of the magnet included in the port 105, and this heating can lead to pain for the patient. The interaction between the MRI and the magnet can also cause movement of the magnet, and this can lead to dislodgement and/or rupture of the tissue expander 100 with in the patient. Moreover, the interaction of the MRI and the magnet and/or the metal structure of the port 105 can cause unwanted artifacts in the output of the MRI. For these reasons, tissue expanders with metal ports and magnets are contra-indicated for use with MRI systems.

Figure 5:
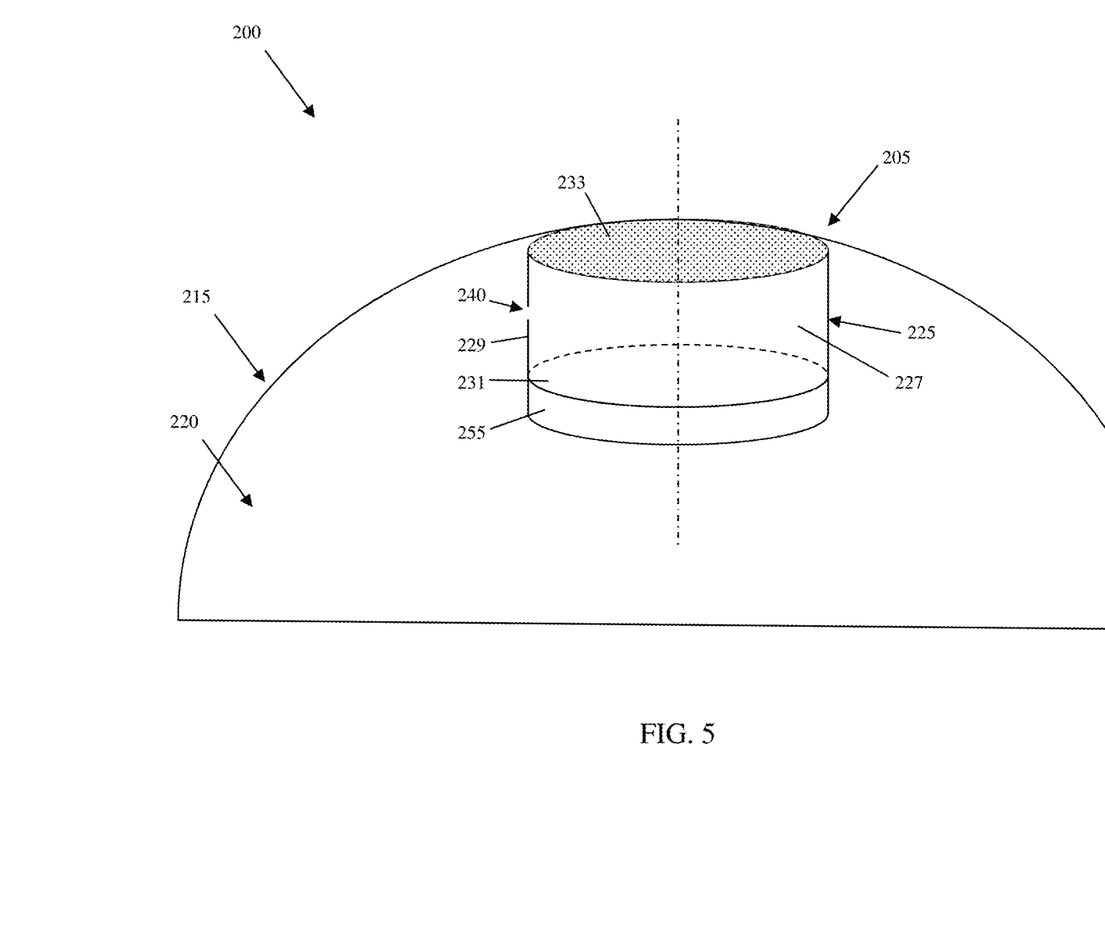
FIG. 5 shows a tissue expander including a access port in accordance with aspects of the invention.

FIG. 5 shows a tissue expander 200 including an access port 205 in accordance with aspects of the invention. In embodiments, the tissue expander 200 includes a shell 215 that defines an interior volume 220 that can be selectively inflated and deflated via the access port 205 in a conventional manner. In embodiments, the access port 205 includes a body 225 that defines an interior volume 227. For illustration, the body 225 is described herein in the shape of a cylinder; however, implementations of the invention are not limited to a cylinder, and instead the body 225 may have any suitable shape and configuration that are capable of performing the functions described herein. In embodiments, the body 225 includes a sidewall 229 and a base 231 at a first end. In embodiments, the access port 205 includes a membrane 233 at a second end of the body 225 opposite the first end. The membrane 233 may be a conventional or later-developed self-healing/sealing material that, after being punctured by a needle of a fluid delivery system (e.g., fluid delivery system 120), reforms an airtight and liquid tight seal. In this manner, the sidewall 229, the base 231, and the membrane 233 define the interior volume 227 of the body 225. The shell 215 may be the same as or similar to the shell 115, and the access port 205 may be configured to perform inflating and/or deflating functions similar to those described with respect to access port 105

In embodiments, the sidewall 229 includes at least one aperture 240 that provides fluid communication between the interior volume 227 of the access port 205 and the interior volume 220 of the shell 215. In this manner, a fluid delivery system (e.g., fluid delivery system 120 of FIGS. 1 and 2) may be used to selectively inflate and deflate the shell 215 in a conventional manner, e.g., by piercing the membrane with a needle 130 and creating a pressure differential with a syringe 150 to cause fluid to flow into or out of the tissue expander 200 via the at least one aperture 240.

According to aspects of the invention, the body 225 including the sidewall 229 and the base 231 is constructed of material that is non-reactive with an MRI. For example, the body 225 may be composed of one or more non-metallic and non-ferromagnetic materials such as one or more polymers. In embodiments, the material of the body 225 is sufficiently rigid to prevent puncture by a needle (e.g., needle 130) of a fluid delivery system (e.g., fluid delivery system 120). In this manner, when a needle of a fluid delivery system is pushed through the membrane 233, the sidewall 229 and the base 231 function as a hard-stop that limit the travel of the needle within the tissue expander 200. A specific example of a material that may be used for the body 225 is Delrin (e.g., polyoxymethylene); although implementations of the invention are not limited to this example, and other materials that are non-reactive with an MRI may be used. Although less preferable than non-metallic material, the body 225 may be composed of metallic material(s) that are non-ferromagnetic, including but not limited to: commercially pure titanium (CP Titanium), Ti-6Al-4V alloy, Ti-6Al-7Nb alloy, Co—Cr alloys (ASTM F75, F562, and F90), and tantalum.

With continued reference to FIG. 5, the port 205 according to aspects of the invention includes a structure 255 that is configured to have a rate of temperature change lower than that of the tissue surrounding the tissue expander 200, such that the structure 255 is temporarily at a different temperature than that of the surrounding tissue when external cooling is applied to the surrounding tissue. In this manner, due to the structure 255 and the surrounding tissue being at different temperatures, the structure 255 may be locatable using an infrared sensor that is external to the patient in which the tissue expander is implanted.

In embodiments, structure 255 is configured to have a rate of temperature change lower than that of the tissue surrounding the tissue expander 200 by being composed of material(s) having a heat capacity (or a specific heat capacity) that is higher than the nominal heat capacity (or the nominal specific heat capacity) of the human body. Heat capacity or thermal capacity is a measurable physical quantity equal to the ratio of the heat added to (or removed from) an object to the resulting temperature change. Heat capacity is an extensive property of matter, meaning that it is proportional to the size of the system. Specific heat capacity (also called specific heat) is the amount of heat needed to raise the temperature of one kilogram of mass by 1 kelvin. Specific heat capacity is an intensive property and is the heat capacity per unit mass of a material. The specific heat capacity of human tissue is nominally given as 3.47 kJ/(kg*K).

By constructing the structure 255 of a material (or a combination of materials) that has a heat capacity (or a specific heat capacity) that is higher than the nominal heat capacity (or the nominal specific heat capacity) of the human body, the structure 255 will exhibit a slower rate of cooling than that of the patient tissue surrounding the implanted tissue expander 200. In this manner, after the tissue expander 200 is brought into thermal equilibrium with the surrounding tissue, the surrounding tissue may be cooled (e.g., by applying a cold compress on the external surface of the patient skin near the tissue expander). As a result of such cooling, and because the structure 255 is configured to cool at a rate slower than that of tissue, there is a period of time when the surrounding tissue is at a different (lower) temperature than that of the structure 255 of the tissue expander.

During this time period, the medical professional may use an infrared sensor (such as a forward looking infrared (FLIR) camera device) to detect the structure 255 of the tissue expander 200 even though the tissue expander 200 is under the skin of a patient (i.e., implanted under the skin and not visible to the naked eye).

In a particular preferred embodiment, the structure 255 not only has a rate of temperature change lower than that of the tissue surrounding the tissue expander 200, but also has a rate of temperature change lower than that of other portions of the tissue expander 200. This may be achieved, for example, by constructing the structure 255 of a material different than that of the remainder of the tissue expander 200. In this manner, when viewed through the patient skin using a FLIR camera, the structure 255 is visually distinguishable from both the patient tissue and the other portions of the tissue expander, and this visual distinctiveness assists the medical professional in aiming the needle 130 through the patient's skin to the membrane 233 of the port 205.

Implementations of the invention are not limited to a particular material for structure 255, and any suitable material or combination of materials may be used for the structure 255 so long as the structure 255 has a rate of temperature change lower than that of the tissue surrounding the tissue expander 200. Moreover, the structure 255 may have any desired shape relative to the entirety of the tissue expander. In a first non-limiting example, the structure 255 has the shape of a disc that is coaxial with membrane 233 and that has substantially a same diameter as that of the membrane 233. In another non-limiting example, the structure 255 has the shape of a ring that is coaxial with membrane 233 and that has an inner diameter that is less than the diameter of the membrane 233. In another example, the structure 255 comprises the entire body 225 including the sidewalls 229 and the base 231. Other shapes and configurations of the structure 255 may be used with embodiments of the invention.

The structure 255 may be part of the body 225 (e.g., integrally molded with the sidewall 229 and the base 231), or alternatively may be connected to the body 225 (e.g., adhered or fused to the base 231), or alternatively may be the body 225. The structure 255 may be composed of the same material as the body 225, or may be composed of a different material that is still non-reactive with an MRI. In embodiments, the structure 255 is centered in the port 205 to facilitate aiming the needle to the membrane 233 for selectively inflating and deflating the tissue expander 200. For example, the structure 255, the body 225, and the membrane 233 may be coaxial along axis 250 as depicted in FIG. 5.

Figure 6:
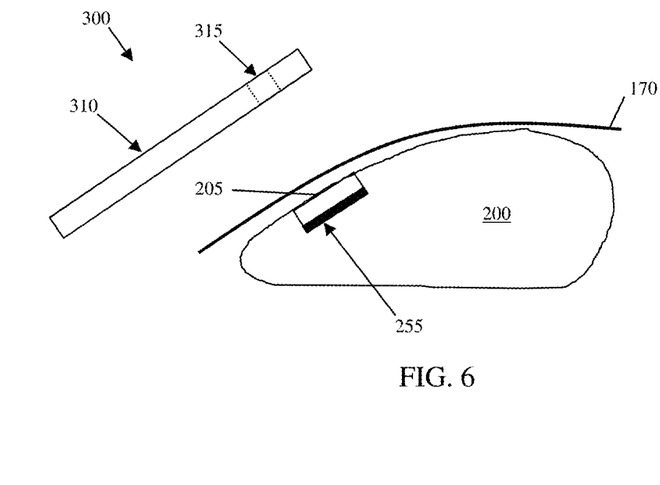
FIGS. 6 and 7A-C show a device configured to detect a port in accordance with aspects of the invention.

FIG. 6 shows a device 300 configured to detect the structure 255 of the port 205 in accordance with aspects of the invention. In embodiments, the device 300 comprises a portable or a hand held computing device is provided with hardware and software that is structured and arranged to provide an infrared sensor that can be used to locate the structure 255 of a port 205 of a tissue expander 200 that is under the skin of a patient (i.e., implanted under the skin, not visible to the naked eye), and display a location of the structure 255 on a visual display of the computing device. The device 300 may comprise a housing, a display 310, and a sensor 315. The housing may house computer components including but not limited to a computer memory, a computer processor, and a power supply. The memory may store program code that is executed by the processor to perform one or more of the functions described herein, including but not limited to controlling the output of the display based on signals received from the sensor. The display 310 may be any desired type of visual display including but not limited to, LCD, LED, etc. In one exemplary embodiment, the device 300 is a FLIR camera device in which an infrared sensor 315 and the display 310 are integrated in a single device. In another exemplary embodiment, the device 300 is a smartphone (e.g., an iPhone) that has an attached FLIR accessory, wherein the FLIR accessory comprises the infrared sensor 315 and the smartphone comprises the display 310 that visually displays the output of the infrared sensor.

Figure 7A:
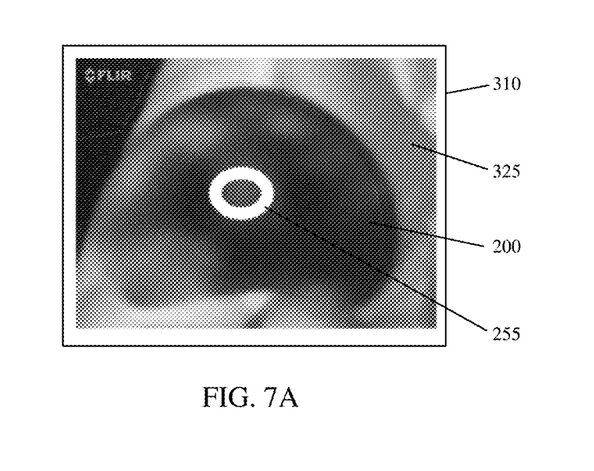
Figure 7B:
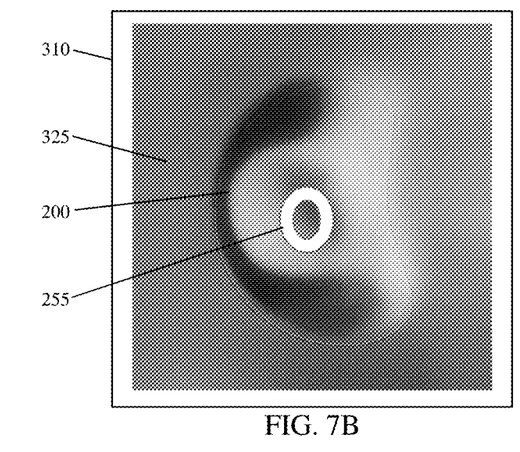
Figure 7C:
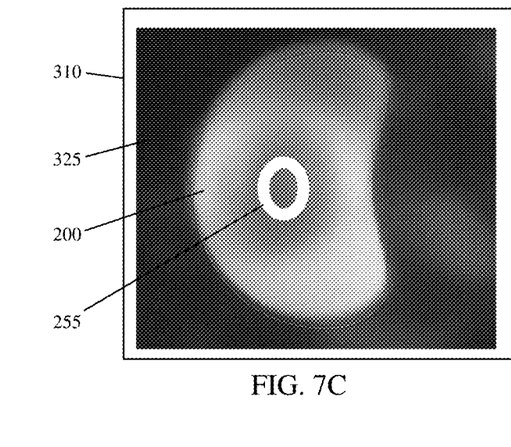

FIGS. 7A, 7B, and 7C show example outputs of the display 310 of the device 300 showing infrared imagery of implanted tissue expanders 200 (i.e., that are under the patient's skin and not visible to the naked eye). As depicted in FIGS. 7A-C, the structure 255 of the port 205 is visually distinguishable from both the patient tissue 325 and the other portions of the tissue expander 200, due to the structure 255 being constructed of materials that have a different rate of cooling than both the surrounding tissue 325 and the other parts of the tissue expander 200.

The access port 205 and structure 255 as described herein may be incorporated into conventional tissue expanders, such as those described in: U.S. Pat. No. 4,800,901; U.S. Patent Publication No. 2007/0233273; U.S. Pat. Nos. 6,666,893; 6,206,930; 7,575,597; 8,454,690, and U.S. Patent Publication No. 2016/0250017, the disclosures of all of which are incorporated by reference herein in their entirety. A tissue expander in accordance with aspects of the invention may include the access port 205 and structure 255 as described herein in combination with features, components, or characteristics of other implants such as those described in the aforementioned patents and patent publications.

Additional aspects of the invention include manufacturing a tissue expander with the access port 205 and structure 255 as described herein. Additional aspects of the invention include a system comprising the port 205 and structure 255 as described herein, separate from a tissue expander, and associated methods of manufacturing the port 205 and structure 255 separate from a tissue expander. Further aspects of the invention include manufacturing and/or using the device 300 as described herein. Even further aspects of the invention include providing instructions for using the device 300 and a tissue expander having access port 205 and structure 255 described herein. The instructions may be at least one of printed and video.

Additional aspects of the invention include a method of using the structure to locate the port of an implanted tissue expander. At step 401, the structure 255 is permitted to come into thermal equilibrium with the surrounding tissue 325 at a first temperature. This may comprise letting the patient sit for a time period with no external cooling on the site of the tissue expander, such that the tissue expander and the surrounding tissue are at the same temperature. At step 402, external cooling is applied to the patient to cool the surrounding tissue to a second temperature. This may comprise placing a cold compress or an ice pack on the skin of the patient over the site of the implanted tissue expander (e.g., on the external surface of the breast of the patient in which the tissue expander is implanted). The external cooling causes the tissue surrounding the tissue expander to cool down relative to the first temperature. Due to the structure 255 having a slower rate of cooling than that of the surrounding tissue, the structure 255 has a temperature different than that of the surrounding tissue for a time during and after the external cooling. At step 403, the external cooling is removed. This may include removing the cold compress or ice pack from the skin of the patient. Due to the structure 255 having a slower rate of cooling than that of the surrounding tissue, the structure 255 will continue to have a temperature different than that of the surrounding tissue for a time after the removal of the external cooling. At step 404, a user uses the device 300 to detect the structure 255 using infrared vision. This may be performed similar to the manner described with respect to FIGS. 6 and 7A-C. At step 405, the user (or another user) inserts a needle 130 into the port 205 using the infrared vision displayed on the device 300 as a guide for locating the port 205 under the skin of the patient.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed:

1. A tissue expander, comprising:
   a selectively inflatable and deflatable shell that is configured to be implanted; and
   an access port for selectively inflating and deflating the shell, the access port comprising a sidewall, a base at a first end, and a membrane at a second end opposite the first end,
   wherein the sidewall and the base of the access port are constructed of a material that is non-reactive with a magnetic resonance imaging (MRI) machine; and
   a structure of the access port is composed of a material that has a rate of temperature change lower than that of human tissue.

2. The tissue expander of claim 1, wherein the material is a non-metallic and non-ferromagnetic material.

3. The tissue expander of claim 1, wherein the material is a non-metallic and non-ferromagnetic polymer.

4. The tissue expander of claim 1, wherein the material is has a heat capacity that is higher than the nominal heat capacity of the human body.

5. The tissue expander of claim 4, wherein the material is has a heat capacity that is different than a heat capacity of other portions of the tissue expander.

6. The tissue expander of claim 1, wherein the material is has a specific heat capacity that is higher than the nominal specific heat capacity of the human body.

7. The tissue expander of claim 6, wherein the material is has a specific heat capacity that is higher than the nominal specific heat capacity of the human body.

8. The tissue expander of claim 1, wherein:
   the membrane is pierceable by a needle; and
   the sidewall and the base function as a hard-stop that limit travel of the needle within access port after the needle has pierced the membrane.

9. A tissue expander, comprising:
   a selectively inflatable and deflatable shell that is configured to be implanted; and an access port for selectively inflating and deflating the shell, the access port comprising a sidewall, a base at a first end, and a membrane at a second end opposite the first end, wherein the sidewall and the base of the access port are constructed of a material that is non-reactive with a magnetic resonance imaging (MRI) machine; and a structure of the access port comprises a portion having a specific heat capacity greater than 3.47 kJ/(kg*K).

10. A method, comprising:

bringing a tissue expander into thermal equilibrium with surrounding tissue in which the tissue expander is implanted, wherein the tissue expander comprises: a selectively inflatable and deflatable shell that is configured to be implanted; and an access port for selectively inflating and deflating the shell, the access port comprising a sidewall, a base at a first end, and a membrane at a second end opposite the first end, wherein the sidewall and the base of the access port are constructed of a material that is non-reactive with a magnetic resonance imaging (MRI) machine, and a structure of the access port is composed of a material that has a rate of temperature change lower than that of human tissue;

applying external cooling to the surrounding tissue;

based on the external cooling, detecting the structure using an infrared sensor; and inserting a needle into the access port while using the infrared sensor as a guide.

\* \* \* \* \*